US012012586B2

(12) United States Patent
Nguyen et al.

(10) Patent No.: US 12,012,586 B2
(45) Date of Patent: Jun. 18, 2024

(54) AUTOMATED GAS CONTROL HYPOXIC CHAMBER FOR MONITORING OXYGEN CONCENTRATION

(71) Applicant: BOARD OF REGENTS, THE UNIVERSITY OF TEXAS SYSTEM, Austin, TX (US)

(72) Inventors: Kytai Truong Nguyen, Arlington, TX (US); Alan Nguyen, Arlington, TX (US); Harish Ramachandramoorthy, Arlington, TX (US); Daniel To, Arlington, TX (US); Dylan Yu, Arlington, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 903 days.

(21) Appl. No.: 17/084,197

(22) Filed: Oct. 29, 2020

(65) Prior Publication Data

US 2021/0348110 A1 Nov. 11, 2021

Related U.S. Application Data

(60) Provisional application No. 62/928,873, filed on Oct. 31, 2019.

(51) Int. Cl.
| | |
|---|---|
| C12M 3/00 | (2006.01) |
| C12M 1/00 | (2006.01) |
| C12M 1/34 | (2006.01) |
| C12M 1/36 | (2006.01) |
| G05D 11/13 | (2006.01) |

(52) U.S. Cl.
CPC ............ *C12M 41/34* (2013.01); *C12M 23/38* (2013.01); *C12M 41/48* (2013.01); *G05D 11/138* (2013.01)

(58) Field of Classification Search
CPC ....... C12M 23/38; C12M 41/48; C12M 41/34
See application file for complete search history.

(56) References Cited

U.S. PATENT DOCUMENTS

| | | | | |
|---|---|---|---|---|
| 2015/0093740 A1* | 4/2015 | Swanda | ................. | C12M 37/00 435/286.1 |
| 2017/0306278 A1* | 10/2017 | Nguyen | ................. | C12M 35/08 |

(Continued)

OTHER PUBLICATIONS

Technical Data Sheet: Eppendorf Cell Culture Plate, 6 Well, 2013, pp. 1-2.

(Continued)

*Primary Examiner* — Nathan A Bowers
(74) *Attorney, Agent, or Firm* — Maynard Nexsen PC; John Zimmer; Candice Cashman

(57) ABSTRACT

A hypoxic chamber system comprises a hypoxic chamber having: a housing, an internal receiving chamber formed within the housing, a lid operably connectable to the housing to seal the receiving chamber in a closed position, a first input and a second input in communication with the receiving chamber, and an oxygen sensor positioned in the receiving chamber; a first regulator valve operatively connected to the first input and an oxygen source; a second regulator valve operatively connected to the second input and a non-oxygen source; and a controller electrically connected to the first regulator valve, the second regulator valve, and the oxygen sensor.

15 Claims, 9 Drawing Sheets

(56) References Cited

U.S. PATENT DOCUMENTS

2019/0330579 A1* 10/2019 Guenat .................. C12M 29/10
2021/0055283 A1*  2/2021 Collins .................. C12M 41/48
2021/0388306 A1* 12/2021 Lim ...................... C12M 41/40

OTHER PUBLICATIONS

Merriam-Webster, Valve Definition & Meaning, pp. 1-12, Accessed Mar. 28, 2024, URL: <https://www.merriam-webster.com/dictionary/valve>.

* cited by examiner

AUTOMATED GAS CONTROL HYPOXIC CHAMBER FOR MONITORING OXYGEN CONCENTRATION

RELATED APPLICATION DATA

The present application claims priority pursuant to 35 U.S.C. § 119(e) to U.S. Provisional Patent Application Ser. No. 62/928,873 filed Oct. 31, 2019 which is incorporated herein by reference in its entirety.

FIELD

The invention is generally related to portable hypoxic chambers for cell growth, and, more specifically, to portable hypoxic chambers that automatically control oxygen levels.

BACKGROUND

In the world or research and academia, cell culture laboratories play a prevalent role. Hypoxic chambers are used in cell culture, specifically cancer research. Hypoxic conditions are mimicked using hypoxic chambers to provide a more realistic environment for cells to thrive. The hypoxic environments that are generated from the hypoxic chambers are becoming increasing relevant and have become an indispensable component of cancer research as they provide a means to study the effects of hypoxia on different cancer cells and their responses.

In a hypoxic environment, cells are not experiencing normal oxygen concentrations such as atmospheric levels, but rather low amounts of oxygen within the body called physoxia. These conditions affect the physiological system of the cells and levels can typically range from a median oxygen content between 3.0% to 7.4%. Often different types of cancer cells prefer hypoxic conditions, such as various lung cancer cells (1.0-2.2%), breast cancer cells (1.3%), and melanoma cells (1.5%).

There are several current hypoxic chamber systems that are commercially available to mimic these hypoxic conditions. As with all products, the products mentioned have specific features that provide either an advantage or a disadvantage when using the product. Representative advantages and disadvantages of these current products are shown in Table 1 and FIGS. 1 and 2 along with the company that manufactures the product and the pricing for the product.

TABLE 1

List of Hypoxic Chambers and Comparable Parameters

| Competitors | Pricing | Advantages/Pros | Disadvantages/Cons |
|---|---|---|---|
| Billups-Rothenberg Inc. | Chamber: $479.00 Flowmeter: $209.00 Modular Oxygen Monitor + $CO_2$ Sensor: Not on market | Fairly cheap and portable Highly durable O-ring for uniform air-tight seal Long lifetime Fits in enclosures Detect both oxygen and carbon dioxide levels | Requires manual purging Unable to determine level of hypoxia No automated functions Not available on market |
| StemCell Technologies | Chamber: $605.00 Flowmeter: $328.00 | 1-year warranty Cylindrical walls to reduce minimize gas flow resistance | Requires manual purging Unable to determine level of hypoxia |
| Bactrox | $23,955.00 | Precise $O_2$ and $CO_2$ control within $1/10^{th}$ of a percent Glove compartment allows work within chamber Constant hypoxic conditions | High pricing Not portable Requires professional maintenance |

As discussed in Table 1, the commercially available hypoxic systems are either cheap and portable, but extremely limited in functionality (no way to measure oxygen levels), or extremely expensive and not portable. Thus, there is a need for improved hypoxic devices that are both portable and affordable, while offering still offering the ability to measure and control oxygen levels, especially automated oxygen level control.

SUMMARY

In an aspect, a hypoxic chamber system comprises a hypoxic chamber having: a housing, an internal receiving chamber formed within the housing, a lid operably connectable to the housing to seal the receiving chamber in a closed position, a first input and a second input in communication with the receiving chamber, and an oxygen sensor positioned in the receiving chamber; a first regulator valve operatively connected to the first input and an oxygen source; a second regulator valve operatively connected to the second input and a non-oxygen source; and a controller electrically connected to the first regulator valve, the second regulator valve, and the oxygen sensor.

In some embodiments, the first regulator valve and second regulator valve are electronically actuated, such as through the use of a solenoid. Electronic actuation of the first regulator valve and the second regulator valve is controlled by the controller. In some cases, the controller electronically actuates the first regulator valve and/or the second regulator valve in response to oxygen sensor readings of an oxygen level in the receiving chamber. In some instances, the controller electronically actuates the first regulator valve to increase oxygen levels in the receiving chamber. The controller electronically actuates the second regulator to decrease oxygen levels in the receiving chamber in other instances. The first regulator valve and the second regulator valve can be wired directly to the controller or wireless controlled by the controller, such as through Bluetooth or Wifi.

In some embodiments, the controller can programmed with a predetermined oxygen level that is entered by a user. The controller can electronically actuate the first regulator valve upon oxygen levels in the receiving space being sensed by the oxygen sensor as being below the predetermined oxygen level, and actuate the second regulator valve upon oxygen levels in the receiving space being sensed by the oxygen sensor as being above the predetermined oxygen level.

In some embodiments, the controller further comprises a graphic user interface ("GUI"), such as an LCD, OLED, or other type of known GUI. In some cases the graphic user interface is a touch screen.

The hypoxic chamber can in some instances further comprise a release valve in communication with the receiving chamber. The release valve can be manually activated by a user to purge the receiving chamber atmosphere, or in other cases can be electronically connected to the controller, being electronically active by the controller.

The oxygen source can be a tank, cylinder, or other known gas storage device. In some cases, the oxygen source is a tank comprising oxygen or an oxygen enriched gas. The non-oxygen source can likewise be a tank, cylinder, or other known gas storage device. the non-oxygen source is a tank comprising nitrogen, carbon dioxide, or a combination thereof. Other gas types are also contemplated.

The controller is programmable by a user to set a predetermined oxygen level in the hypoxic chamber receiving space. The controller can continuously monitor oxygen levels in the hypoxic chamber receiving space with the oxygen sensor in some instances. In other instances, the controller monitors oxygen levels in the hypoxic chamber receiving space with the oxygen sensor at predetermined time intervals.

In some embodiments, the controller further comprises an auditory or visual indicator that is activated when the oxygen sensor measures an oxygen level that exceeds or falls below the predetermined oxygen level. Exemplary auditory indicators include a buzzer, speaker, or other auditory signaling device. Exemplary visual indicators include an LED, incandescent, fluorescent, or other light generating devices.

The hypoxic chamber and housing are formed from a polymeric material, such as a thermoplastic polymer. In some cases, the thermoplastic polymer is acrylonitrile butadiene styrene (ABS), a polycarbonate, or a combination of both. In a preferred embodiment, the thermoplastic polymer is structurally stable at 120° C. or greater for at least 30 minutes under saturated steam under at least 10 psi of pressure.

In another aspect, a method of growing cells in a hypoxic environment comprises placing the cells in the receiving space of the receiving chamber of the hypoxic chamber system described herein; setting a predetermined oxygen level for the receiving chamber, and actuating the first regulator valve, second regulator valve, or both to introduce an environment in the receiving chamber having the predetermined oxygen level.

In some embodiments, the method further comprises monitoring oxygen levels in the receiving chamber with the oxygen sensor. In some cases the method further comprises actuating the first regulator valve upon oxygen levels in the receiving space being sensed by the oxygen sensor as being below the predetermined oxygen level. The method can further comprise actuating the second regulator valve upon oxygen levels in the receiving space being sensed by the oxygen sensor as being above the predetermined oxygen level.

DETAILED DESCRIPTION

Figure 1:
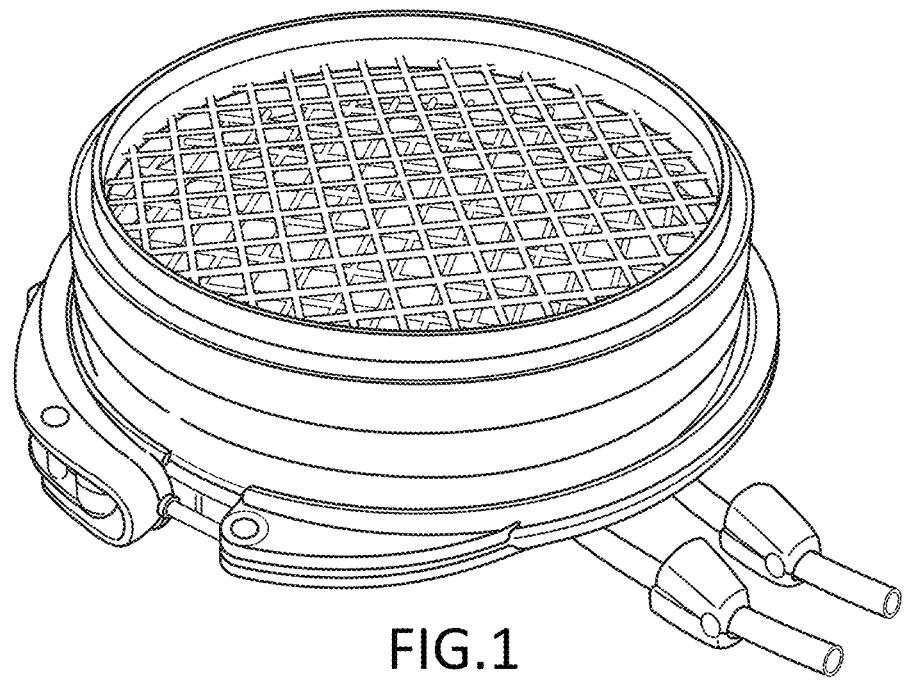
FIG. 1 is a perspective view of a hypoxic chamber commercially available from StemCell Technologies.
Figure 2:
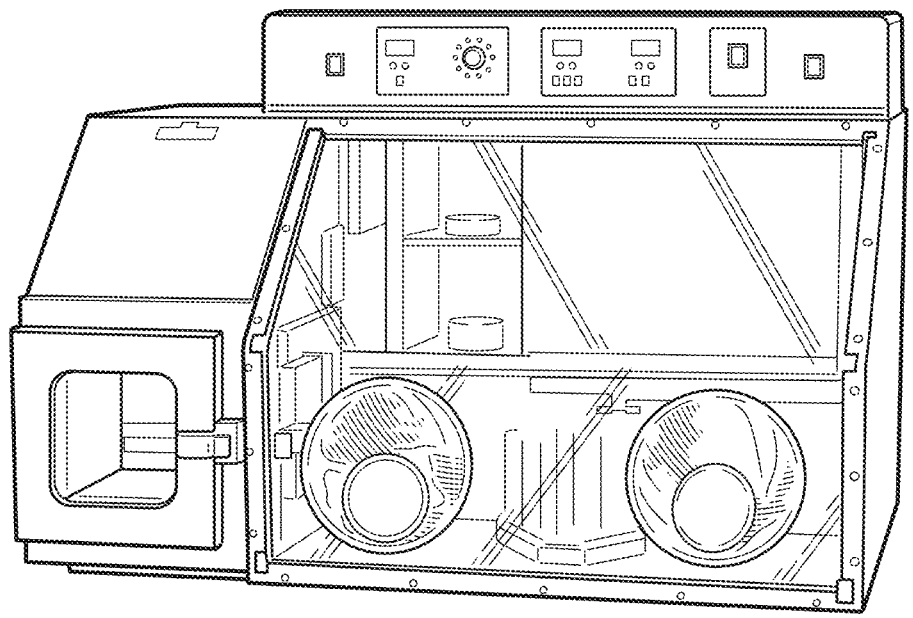
FIG. 2 is a perspective view of a hypoxic chamber system commercially available from Bactrox.

All ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

All ranges disclosed herein are also to be considered to include the end points of the range, unless expressly stated otherwise. For example, a range of "between 5 and 10," "from 5 to 10," or "5-10" should generally be considered to include the end points 5 and 10.

Further, when the phrase "up to" is used in connection with an amount or quantity, it is to be understood that the amount is at least a detectable amount or quantity. For example, a material present in an amount "up to" a specified amount can be present from a detectable amount and up to and including the specified amount.

Described herein are hypoxic chamber systems that are portable, inexpensive, and automated. Generally, systems described herein comprise a hypoxic chamber with an oxygen sensor, a controller to intake data readings from the sensor, and to control various valves for automatic purging and introduction of desired gases.

In some instances, systems and methods described herein can aid researchers in both industry and academia in cell culture research using hypoxic conditions. Optionally equipped with an alert system, a user can be aware of any potential or active deviations occurring within the hypoxia chamber. Real-time monitoring of the oxygen levels within the hypoxia chambers allows for active readings to be observed. The automatic purging system automates the atmospheric monitoring system, allowing for dynamic, real-time control of the oxygen levels inside the hypoxic chamber. In various embodiments, the purging system controls a singular tank mixture, such as oxygen, nitrogen, and carbon dioxide, or a dual tank setup, with one tank being dedicated to an oxygen source. Furthermore, the systems described herein have a small form factor, allowing them to be easily portable II. Hypoxic Chamber Systems In one embodiment, a hypoxic chamber is disclosed. In one aspect of this embodiment, the hypoxic chamber allows a user to mimic the in-vivo conditions of the human body by controlling the oxygen content present, and allow access for users to analyze cells, such as cancer cells, which are grown in the chamber.

In one aspect, a hypoxic chamber system comprises a hypoxic chamber, a first regulator valve, a second regulator valve, and a controller. The hypoxic chamber can comprise a housing, an internal receiving chamber formed within the housing, a lid operably connectable to the housing to seal the receiving chamber in a closed position, a first input and a second input in communication with the receiving chamber, and an oxygen sensor positioned in the receiving chamber. In some embodiments, the hypoxic chamber further comprises a release valve in communication with the receiving chamber, for venting of the atmosphere in the receiving chamber. The release valve can be manually or electronically activated.

The housing and lid can be formed from any material not inconsistent with the objectives of this disclosure. For instance, the housing and lid can be made of a material that is structurally stable at 120° C. or greater for at least 30 minutes under saturated steam under at least 10 psi of pressure. In other words, the housing and lid can be formed from a material that can be sterilized by a steam autoclave. In some cases, the housing are formed from a thermoplastic polymer. In some embodiments, the thermoplastic polymer is acrylonitrile butadiene styrene (ABS), a polycarbonate, or a combination of both.

The first regulator valve is operatively connected to the first input of the hypoxic chamber, and an oxygen source. The oxygen source can be any container, tank, cylinder, or the like that is used in the art to store gases or gas sources (such as liquefied gasses). In some cases the oxygen source comprising 100% oxygen, or in other cases comprises an oxygen enriched gas.

The second regulator valve is operatively connected to the second input and a non-oxygen source. The non-oxygen source can be any container, tank, cylinder, or the like that is used in the art to store gases or gas sources (such as liquefied gasses). In some embodiments, the non-oxygen source comprises nitrogen, carbon dioxide, or a combination thereof.

The controller can be a microcontroller or any controller not inconsistent with the objectives of this disclosure. The controller can comprise a microcontroller; a non-volatile memory that stores instructions for controlling one, two, three, or more regulator values, instructions for communicating with an oxygen sensor, instructions for activating an indicator, instructions for communicating with a temperature sensor, or any other instructions for communicating with the various features of the hypoxic chamber system described herein. In some cases, the controller further comprises or is operatively connected to a graphic user interface. The graphic user interface (GUI) can be a touch screen, or a monitor. When the GUI is a monitor, the controller can also be operatively connected to keyboard, various operational buttons, or other similar data entry devices.

In some embodiments, the controller is electrically connected to the first regulator valve, the second regulator valve, the oxygen sensor, and optionally to the release valve. The first regulator valve and second regulator valve can be electronically actuated in some cases, and electronic actuation of the first regulator valve and the second regulator valve can be controlled by the controller. Exemplary electronic actuating devices for the first and second regulator valves include a solenoid actuator, a relay-based actuator, and the like. The first regulator valve, the second regulator valve and the oxygen sensor can be electronically connected to the controller via a wired or a wireless connection, or a combination of both. Exemplary wireless connections include Bluetooth™, wifi, radiowaves, or any other wireless connection known in the art.

The controller can electronically actuate the first regulator valve and/or the second regulator valve in response to oxygen sensor readings of an oxygen level in the receiving chamber. In some cases, the controller electronically actuates the first regulator valve to increase oxygen levels in the receiving chamber. In some instances, the controller electronically actuates the second regulator to decrease oxygen levels in the receiving chamber.

The controller can be programmed by a user to set a predetermined oxygen level in the hypoxic chamber receiving space using the touch screen or data input device. This predetermined oxygen level can be a single concentration percentage (e.g. 1%), or can be a range (e.g. 1-1.3%). In some embodiments, the controller electronically actuates the first regulator valve upon oxygen levels in the receiving space being sensed by the oxygen sensor as being below the predetermined oxygen level. In some embodiments, the controller electronically actuates the second regulator valve upon oxygen levels in the receiving space being sensed by the oxygen sensor as being above the predetermined oxygen level. Thus, hypoxic chamber systems described herein can automatically monitor and regulate an oxygen content present in a hypoxic chamber.

The controller can continuously monitor oxygen levels in the hypoxic chamber receiving space with the oxygen sensor, or can monitor oxygen levels in the hypoxic chamber receiving space with the oxygen sensor at predetermined time intervals, such as every second, 5 seconds, 10, seconds, 30 seconds, 1 minute, 2 minutes, 5 minutes, 10 minutes, or at intervals of greater than 10 minutes.

In some embodiments, the controller further comprises an auditory or visual indicator that is activated when the oxygen sensor measures an oxygen level that exceeds or falls below the predetermined oxygen level. A user can be alerted to the presence of oxygen at levels outside the predetermined oxygen level set by the user by activation of the indicator.

In some embodiments, the controller has a small form factor, and can fit in a small and easily portable housing, such as in a housing having a maximum volume of a 12.7 cm (5 in) cube. In some cases, the first and second valve regulators can be integrated into the same housing as the controller, making the controller and first and second valve regulators an integrated device that is easily portable.

II. Methods of Growing Cells In A Hypoxic Environment

In another aspect, a method of growing cells in a hypoxic environment is contemplated comprising placing the cells in the receiving space of the receiving chamber of the hypoxic chamber system described in Section I herein; setting a predetermined oxygen level for the receiving chamber, and actuating the first regulator valve, second regulator valve, or both to introduce an environment in the receiving chamber having the predetermined oxygen level.

The predetermined oxygen level can be set by a user using the touchscreen or data input device connected to the controller, or can be a preset option preprogrammed into the controller.

In some embodiments, the method can further comprise monitoring oxygen levels in the receiving chamber with the oxygen sensor. The oxygen levels can be continuously monitored or can be monitored at preprogrammed or user specified time intervals.

The method can further comprise actuating the first regulator valve upon oxygen levels in the receiving space being sensed by the oxygen sensor as being below the predetermined oxygen level; and actuating the second regulator valve upon oxygen levels in the receiving space being sensed by the oxygen sensor as being above the predetermined oxygen level. The actuation of the first and second regulator valves can be automatically performed by the controller, or in some cases, can be manually activated by a user.

The embodiments described herein can be understood more readily by reference to the following Examples. Elements, apparatus and methods described herein, however, are not limited to the specific embodiments presented in the Examples. It should be recognized that these sections describe embodiments and examples that are merely illustrative of the principles of this disclosure. Numerous modifications and adaptations will be readily apparent to those of skill in the art without departing from the spirit and scope of the disclosure.

Example 1

Hypoxic Chamber System Specifications

Oxygen Sensing Component

Ideally, the device's oxygen sensing component is accurate to #1% in measuring oxygen concentration levels. One representative oxygen sensor is the LuminOx oxygen sensor (SST Sensing), which has a manufacturer's accuracy of >2% FS (full scale). The accuracy of the oxygen sensor can be calibrated using standards for the gases that the company, SST Sensing, used when manufacturing the oxygen sensor. With a 2% FS accuracy, the sensor is accurate to 2% of the full-scale measurement of the system. Since the sensor has a full measurement of up to 25%, the accuracy reading will be within 2% of 25%, meaning that at every oxygen reading the accuracy of the sensor will be within +0.5% of the actual oxygen concentration.

Signaling Changes in Oxygen Concentration

The oxygen sensor measures oxygen concentration within the hypoxic chamber. When the oxygen concentration exceeds or falls below certain threshold levels, it can be important to alert a user, so the user can adjust the oxygen levels within the chamber. A user can be alerted, for example, using auditory and/or visual signals.

In some embodiments, an LED light and/or a buzzer are used to provide auditory and/or visual alerts to notify a user that oxygen concentrations fall outside pre-determined thresholds.

The time response of the system can also a relevant feature, since the device relies on the measurements from the oxygen sensor. In one aspect, the time response is a T90 type of response, which means that the sensor reads the measurement when 90% of the reading is measured.

Hypoxic Chamber Physical Specifications

It can be advantageous for the hypoxic chamber to also include various physical specifications. In one embodiment, the device is no larger than 5 in ×5 in ×5 in (12.7 cm) in measurements on each side, although it is noted that this dimension is entirely arbitrary and in other examples, can be any other size desired or limited by the size of the components used in the controller.

The hypoxic chamber device should be able to withstand hypoxic conditions, which means that the fabricated device needs to be able to withstand at least 35° C. in temperature and 90-95% humidity. These conditions can be used in conjunction with the hypoxic chamber device to mimic in vivo condition to more accurately study experiments done with hypoxic conditions.

In some embodiments, the hypoxic chamber device is be easily sterilized, such as through chemical methods or a steam autoclave. This can be beneficial, since the hypoxic chamber device might be exposed to cells used in various experiments using hypoxic conditions. If the device cannot easily be sterilized, future experiments might be compromised due to residual contamination.

Applicable Standards

ISO 17289:2014 is a standard that specifies an optical method for determining the concentration of dissolved oxygen using a sensor based on fluorescence quenching. This measurement can be made as a concentration of oxygen in milligrams per liter, percentage saturation (% dissolved oxygen), or both. Depending of the instrument used, detection limits of 0.1 mg/l or 0.2 mg/l can be reached. Certain sensors permit measurement of values higher than 100%.

In one embodiment, the controller is adapted for use with type A plug-ins into wall outlets. The class II ungrounded plug, with two flat parallel prongs, is standard in most of North and Central America. It is known as NEMA 1-15, the plug has two flat 1.5 mm thick blades, measuring 15.9-18.3 mm in length and spaced 12.7 mm apart. Type A plugs are generally polarized and can only be inserted one way because the blades do not have the same width. The blade connected to neutral is 7.9 mm wide and the hot blade is 6.3 mm wide and the plug is rated at 15 A.

Exemplary Hypoxic Chamber System

In one embodiment, the controlling unit is disposed outside the hypoxic chamber, with wires connecting the oxygen sensor into the chamber, and a valve regulatory system is controlled using another microcontroller. In one aspect of this embodiment, the valve regulatory system is controlled using Bluetooth technology, to avoid any long wire connections, which allows for more portability of the valve system.

The rationale behind this choice is that the controller unit in this design, with only the oxygen sensor going into the chamber, will conserve the most volume inside the hypoxic chamber receiving space. This allows for more cells to be included in any experiment performed using this device.

Depending on the user's preference, the controller unit can be placed inside or outside of the incubator during the experiment.

Figure 4:
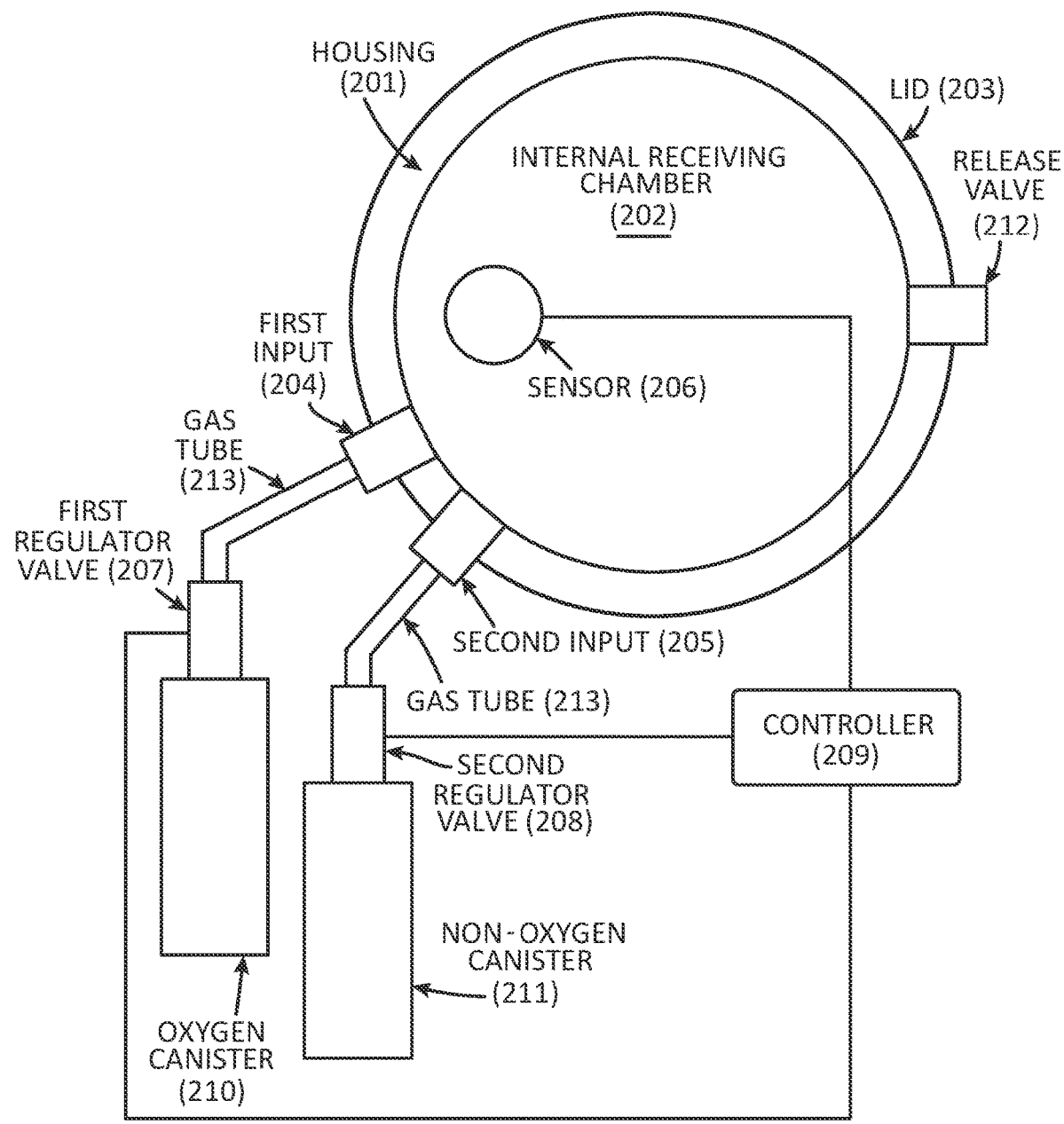
FIG. 4 is a schematic view of a hypoxic chamber system.

In one aspect of this embodiment, the valve system is controlled using Bluetooth to communicate the oxygen readings from a Raspberry Pi to valves programming on the Arduino Uno. In this aspect, the need for physical connecting wires is eliminated, and the location of the valve system can be anywhere within Bluetooth range. Further, this does not restrict the settings of the gas canisters. FIG. 4 shows an exemplary schematic of a hypoxic chamber system. In FIG. 4, a hypoxic chamber system comprises a hypoxic chamber having a housing (201), an internal receiving chamber formed within the housing (202), a lid operably connectable to the housing to seal the receiving chamber in a closed position (203), a first input (204) and a second input (205) in communication with the receiving chamber, and an oxygen sensor (206) positioned in the receiving chamber; a first regulator valve (207) operatively connected to the first input (204) and an oxygen source; a second regulator valve (208) operatively connected to the second input (205) and a non-oxygen source; and a controller electrically connected to the first regulator valve (207), the second regulator valve (208), and the oxygen sensor (206). The oxygen source is an oxygen canister (210). The non-oxygen source is a non-oxygen canister (211) comprising nitrogen, carbon dioxide, or a combination thereof. The hypoxic chamber further comprises a release valve (212) in communication with the receiving chamber. The first regulator valve (207) and the second regulator valve (208) are connected to the first input (204) and second input (205), respectively, through gas tubes (213).

Materials and Components of the Hypoxic Chamber System

The hypoxic chamber system can incorporates several materials and components, including but not limited to those listed in Table 2 below.

Subsystems

The device can contain two major subsystems, the first of which is a Raspberry Pi 3B+ portion of the device, and the second is an Arduino Uno portion of the device. These subsystems are used to show proof of concept, and can in other embodiments be replaced with a dedicated microcontroller and PCB.

Subsystem 1

Figure 3:
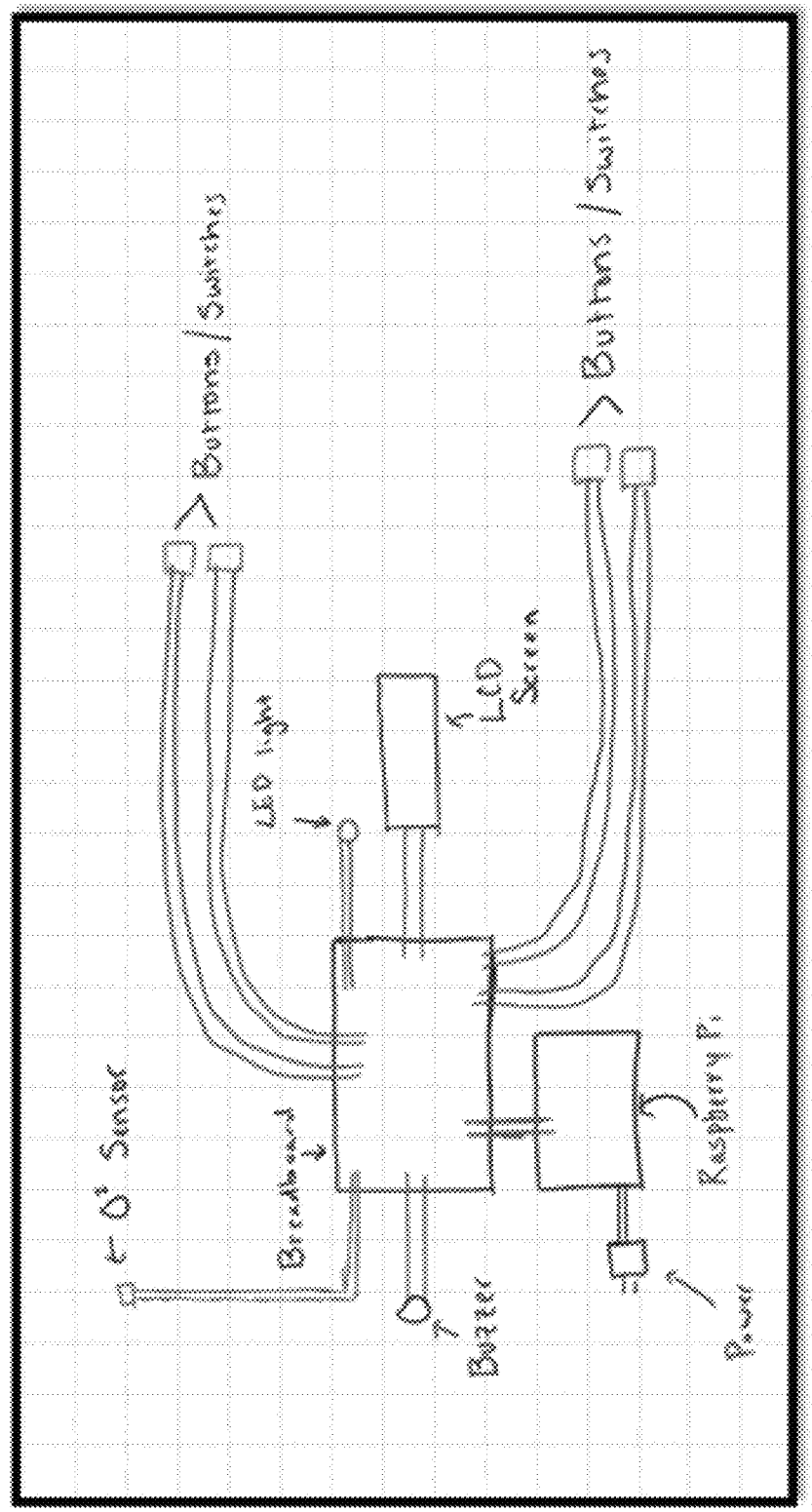
FIG. 3 is a schematic view of a controller used in a hypoxic chamber system.

The first subsystem revolves around using a Raspberry Pi 3B+ acting as the central unit for the device as well as its intended functions. The Pi houses a microSD card containing the program, settings, and code needed for the device to function. Attached to the microcontroller is the LuminOx Oxygen Sensor, the LCD screen, and a PCB. On the PCB are four buttons, an active buzzer, and an LED light. FIG. 3 shows an exemplary schematic of this first subsystem.

Subsystem 2

The second subsystem has Arduino Uno as the microcontroller for this subsystem. Attached to the Uno is a Bluetooth adapter and breadboard. On the breadboard are several resistors and capacitors as well as the wires leading to the valve system that will be attached to their respective gas canisters. The valve system contain the two solenoid valves that will accept the signals sent from the Arduino Uno. It is to be noted that while two subsystems and two microcontrollers are used here (Pi and Uno), it is contemplated that a single microcontroller can also be used to control both subsystems.

Controller Device Programming

The controller runs by executing a python script whenever the Raspberry Pi boots up. The script begins by activating the LuminOx sensor for obtaining oxygen concentration data, and by prompting a user to enter a desired oxygen level

TABLE 2

Materials & Components with a Description of Purpose

| Material/Components | Description of Purpose |
| --- | --- |
| Raspberry Pi 3B+ | One of the microcontrollers used to program and control the sensor, display, and release valve. Contains a microSD card with the program and code for the device. There is Bluetooth connectivity to allow for communication with the other subsystem containing the Arduino. |
| Arduino Uno | One of the microcontrollers used to control the valving system that will be in contact with the gas canister(s). The microcontroller will use a Bluetooth module for added Bluetooth connectivity with the Raspberry Pi 3B+. |
| LuminOx $O_2$ Sensor | The sensor used to measure oxygen levels within the hypoxic chamber. |
| Active Buzzer | The buzzer used to emit an auditory alert when the oxygen level of the chamber is out of a programmable range. |
| LED | The LED lights are used as a visual alert for when the oxygen percentage level of the chamber is out of the programmable range. |
| Jumper Wires (Stranded) | The wires used to connect some of the electrical components. |
| Solid Core Copper Wires | The wires used to replace the jumper cables on the PCB and other jumper wires to reduce clutter in the system. |
| Breadboard | The initial component used as a terminal to connect and power the electronic components to the Raspberry Pi. |
| Printed Circuit Board (PCB) | The replacement component for the breadboard. |
| 12 V Solenoid Valves | The valve used to control the flow rate of the gas to the hypoxic chamber by either opening or closing the valve. |
| Acrylonitrile Butadiene Styrene (ABS) | Thermoplastic polymer used to fabricate the housing unit for the electronics. |
| Heat Shrink Tubing | Tubing that will insulate exposed wires. |
| LCD Screen | The screen will display the oxygen concentration for the user |
| Programmable Buttons | Buttons used to allow the user to set oxygen thresholds |
| Bluetooth Module HC-06 | The Bluetooth module for the Arduino to communicate with the Raspberry Pi. | in the hypoxic chamber receiving space through the LCD screen. Next, the oxygen level is gathered in real-time from the LuminOx and compared to ±0.5% the set $O_2$ level. Should the oxygen level be too high, a signal is sent to the Arduino through Bluetooth to open the valves connected to the mixed gas tank (such as $N_2/CO_2$ to purge the hypoxic chamber. On the other hand, if the oxygen level is too low, a signal is sent to the Arduino to open the valves connected to the $O_2$ tank. Throughout the oxygen sensing process, the system is constantly looking for inputs from the reset button to reset the set $O_2$ level or the off button to turn the device off. The programming process algorithm is presented in FIG. 5.

Figure 5:
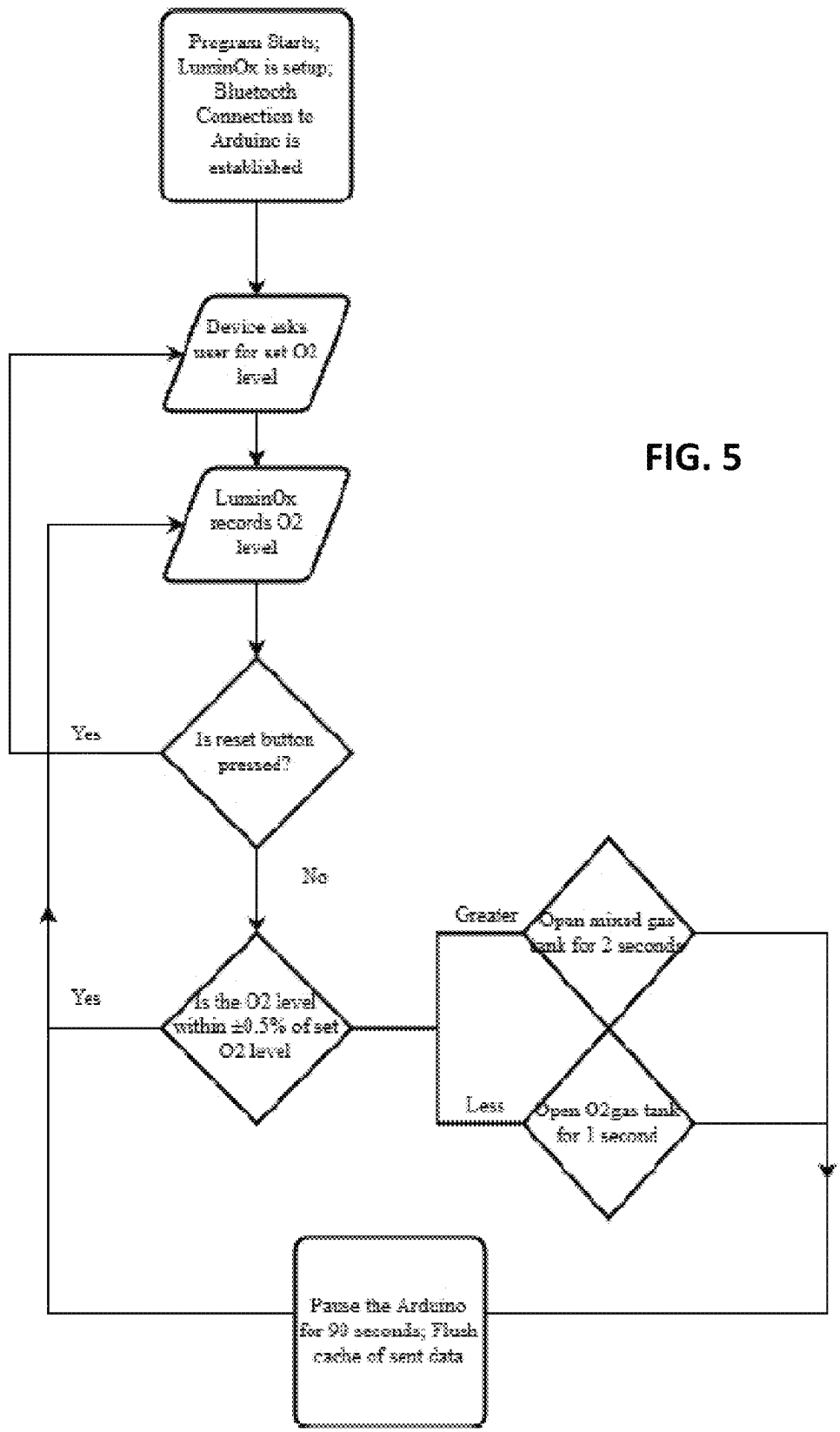
FIG. 5 is a programming process algorithm for automatically controlling an oxygen content in a hypoxic chamber.
Figure 6:
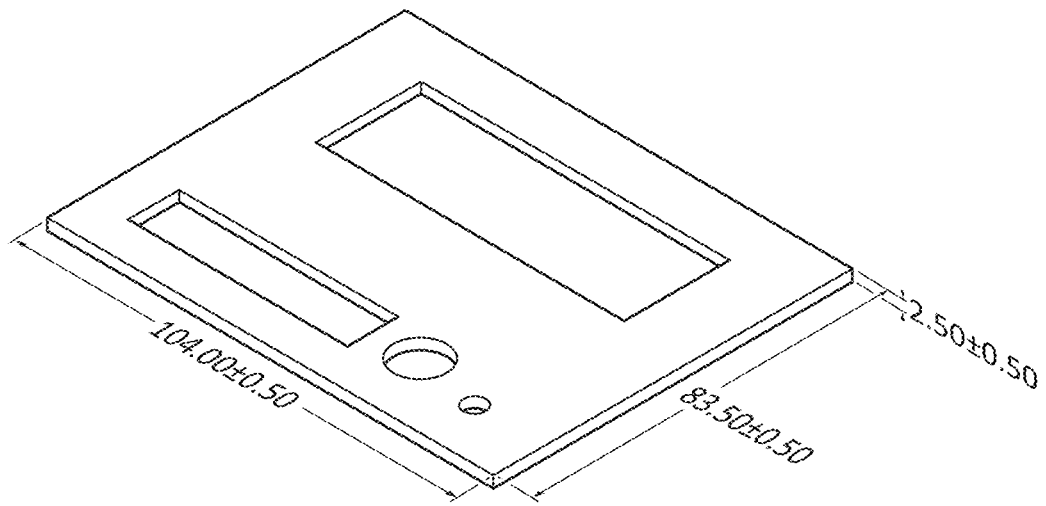
FIG. 6 is a perspective view of a lid for a controller for a hypoxic chamber system.
Figure 7:
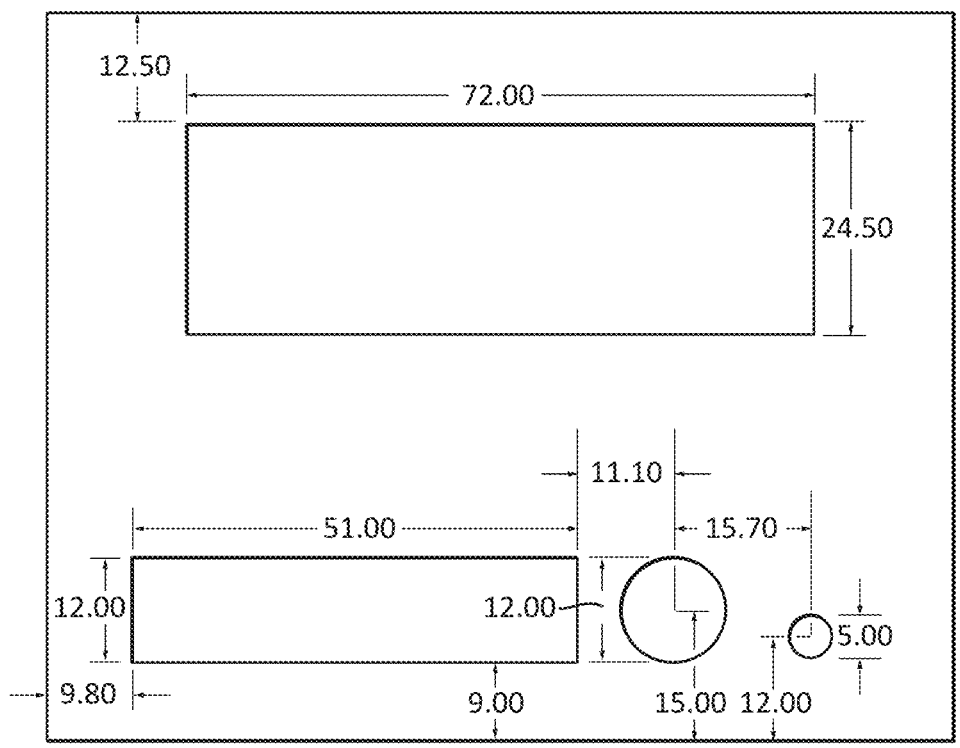
FIG. 7 is a plan view of a side of a controller housing for a hypoxic chamber system.
Figure 8:
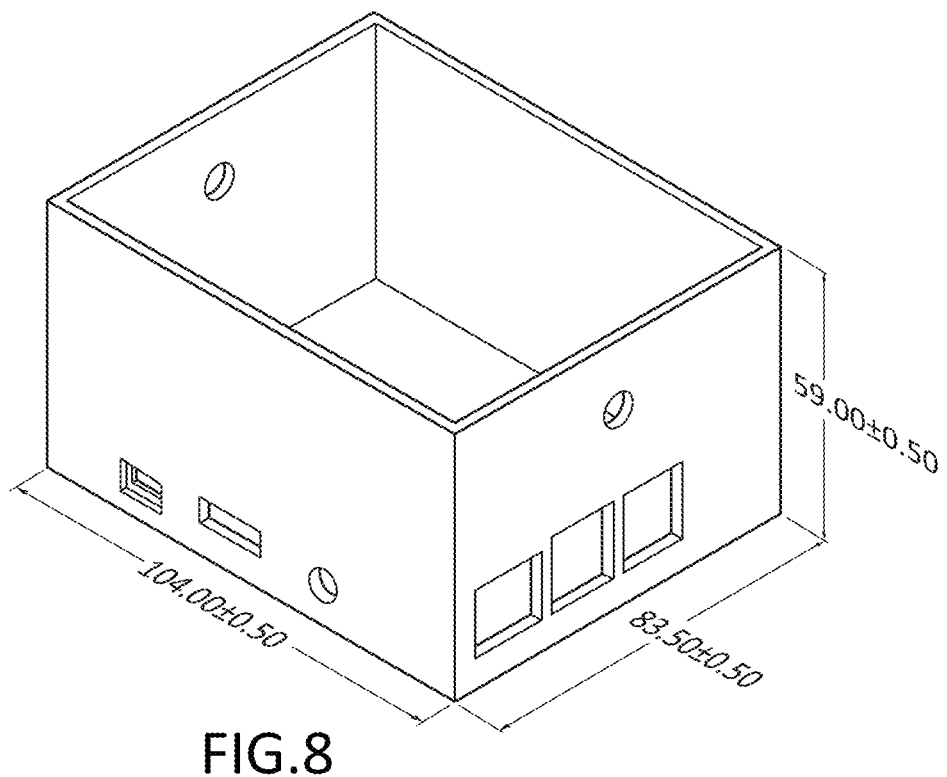
FIG. 8 is a perspective view of the controller housing in FIG. 7.
Figure 9:
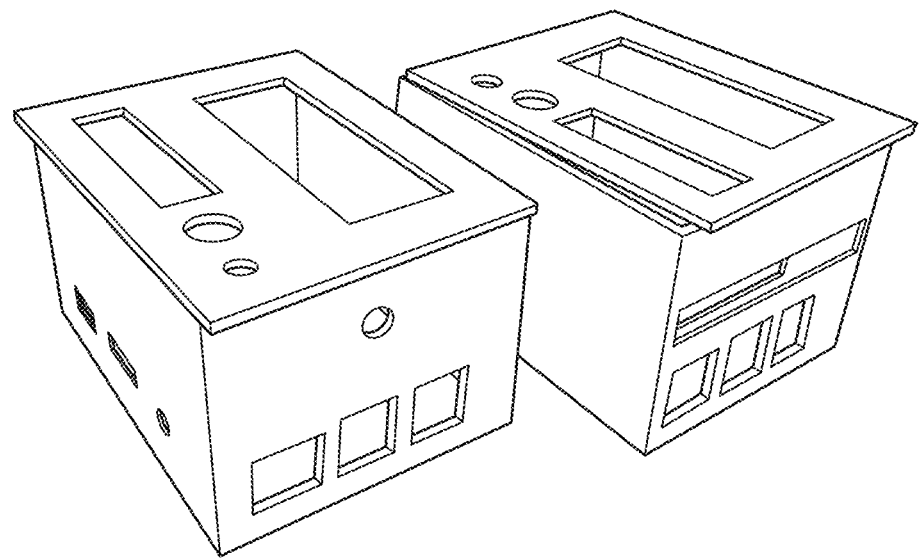
FIG. 9 is a perspective view of two 3D printed controllers having the lid of FIG. 6 and the controller housing of FIG. 7.

As shown in FIG. 5, the program starts, the oxygen sensor is set up, and a Bluetooth connection is established. The user sets an oxygen threshold level on the device, and the oxygen sensor records the oxygen level. If the reset button is not pressed, and this level is more than +0.5% of the threshold level, then a valve is opened to either add oxygen, or add an inert gas. The Arduino is then paused, for example, for 90 seconds, and the cache is flushed of the sent data.

Example 2

Simulation of Flow Rates for Controlling Hypoxic Chamber Atmosphere

The simulations used performed to calculate a flow rate against a time component of the hypoxic chamber system of Example 1. The flow rate determines how long or how wide the diameter of the valve regulator is open. The first component on determining the flow rate required is to set initial conditions for the gas canister. The valve of the gas canister measures in pounds per square inch (psi), therefore the pressure can used to find the flow rate of the gas. The first step is to find the pressure inside the hypoxic chamber and their partial gas pressures. To calculate partial pressures, the volume of the chamber is calculated and then Dalton's Law is used for the pressures.

Volume(cylindrical)=$\pi R^2 \times H$

Let $R$=6 in. and $H$=7 in.

Volume=791.68 in$^3$

Volume Chamber=0.012973 m$^3$

Most of the gas in the atmosphere is comprised of nitrogen, oxygen and carbon dioxide. The gas composition in inside the hypoxic chamber receiving space prior to adding any gas is made up of 78%, 21% and 0.03% of nitrogen, oxygen, and carbon dioxide in atmospheric air respectively. Calculating the volume of each gas inside the chamber is therefore:

Volume$_{Nitrogen}$=Volume$_{Chamber} \times 0.78$=0.0101192 m$^3$

Volume$_{Oxygen}$=Volume$_{Chamber} \times 0.21$=0.0027244 m$^3$

Volume$_{Carbon\ Dioxide}$=Volume$_{Chamber} \times 0.0003$=3.892$\times 10^{-6}$ m$^3$ After calculating the individual volumes of the three gases one can calculate the mass of the gas using the density for each gas.

$$\rho = \frac{m}{V} \rightarrow m = \rho \times V$$

-continued $$\rho_{Nitrogen} = 1.2504 \frac{kg}{m^3}$$

$$\rho_{Oxygen} = 1.429 \frac{kg}{m^3}$$

$$\rho_{Carbon\ Dioxide} = 1.89 \frac{kg}{m^3}$$

$m_{Nitrogen} = 0.012653047$ kg $m_{Oxygen} = 0.003893167$ kg $m_{CarbonDioxide} = 7.35588 \times 10^{-6}$ kg Then, using the volume and mass of the individual gases, the partial pressures can be calculated for each of the gases. Assume that before adding any gases from the canister that the pressure inside the hypoxic chamber is at STP conditions, meaning that the pressure inside the chamber is at a standard 1 atm, which is converted to 101325 Pa. Assuming STP conditions, the mole fractions of each gas are calculated from the mass and the molecular weight of each gas. Using the molecular weight of each gas, weight in grams of each gas is divided by the molecular weight of the gas to obtain the number of moles, which is then added together to get the total moles, and each gases' moles are divided by the total to get the mole fraction.

Nitrogen Gas = $28.013 \frac{g}{mol}$

Oxygen Gas = $32 \frac{g}{mol}$

Carbon Dioxide = $44.01 \frac{g}{mol}$

Moles of N2 = $\frac{(m_{Nitrogen}) \times 1000}{Nitrogen\ Gas}$ = 0.4517 moles N2

Moles of O2 = $\frac{(m_{Oxygen}) \times 1000}{Oxygen\ Gas}$ = 0.1217 moles O2

Moles of CO2 = $\frac{(m_{CarbonDioxide}) \times 1000}{Carbon\ Dioxide}$ = 0.000167 moles CO2

Total Moles = 0.573567 moles

N2 Mole Fraction = $\frac{0.4517}{0.573567}$

O2 Mole Fraction = $\frac{0.1217}{0.573567}$

CO2 Mole Fraction = $\frac{0.000167}{0.573567}$

Partial Pressure of N2=N2 Mole Fraction×101325 Pa=79796.26181 Pa

Partial Pressure of O2=O2 Mole Fraction×101325 Pa=21499.23636 Pa

Partial Pressure of CO2=CO2 Mole Fraction×101325 Pa=29.50182803 Pa

Percent of N2 (%) = $\frac{Partial\ Pressure\ N2}{Total\ Pressure} \times 100$ = 78.7528%

Percent of O2 (%) = $\frac{Partial\ Pressure\ O2}{Total\ Pressure} \times 100$ = 21.2181%

Percent of CO2 (%) = $\frac{Partial\ Pressure\ CO2}{Total\ Pressure} \times 100$ = 0.02912%

The desired percentage of oxygen gas inside the hypoxic chamber ranges from 1-5%. The valve from the gas canister has outputs that measure in pressure (psi), therefore by determining the flow from the canister the time needed for the hypoxic chamber to purge can be calculated. The gas from the canister has a volume of 95/5% nitrogen to carbon dioxide respectively.

The preferred volumetric flow rate for purging the hypoxic chamber is 40 L/min which is equivalent to 0.04 m^3/min. To find the new total pressure, Boyle's Law of $P_1 V_1 = P_2 V_2$ is used, where the initial conditions are set equal to the end conditions (where the volume is known) to find the final pressure.

Example 3

Controller Fabrication

To fabricate the device, several steps were performed to achieve the creation of the device. The first major step was fabrication of the controller unit housing. The casing was created by the 3D Computed-Aided-Design (CAD) program, SolidWorks. The second major step was soldering and wiring of the device.

For the controller unit casing, the team designed the casing dependent of the important ports that were deemed necessary to have exposed. The ports that were deemed necessary were the four USB ports, the Ethernet port, the HDMI and micro-USB ports, and lastly the audio jack ports. First, before opening Solidworks to design the casing measurements were taken on the Raspberry Pi with a caliper to determine spacing and were compare to a schematic sheet from Raspberry Pi's website for accuracy. Then in Solidworks a rectangular box was created using 5 mm thick walls and creating openings at the appropriate locations determined by the measurements with the caliper. Lastly, there were opening is the middle of the two end walls of the casing this allows wire to be put through the holes to allow connection to the oxygen sensor and the outlet valve. The top of the casing was designed by measuring the spacing of the buttons, buzzer, LED and LCD screen that would be displayed to the user. FIGS. 6-9 provide detailed information, including dimensions, of one embodiment of the controller unit casing.

The next component that was fabricated was the circuitry for the controlling system using the Raspberry Pi. The system includes the LCD screen for the display of the oxygen concentration levels, programmable buttons for enabling the user to set thresholds, an active buzzer for audio signals, and a LED light for visual signals. The use of a breadboard was used for the initial prototype and planning of the circuit and was later replaced by a PCB (printed circuit board) to condense and conserve spacing. However, the change from a breadboard to a PCB dictated soldering the wires to PCB instead of simply placing the wires inside the openings on a solderless breadboard.

The solder used for the soldering of the wires was a lead-based solder which was heated to approximately 600 degrees Fahrenheit which was melted. With the use of the soldering iron tip, the melted solder was applied onto the PCB where the wires were connected. Initially, the wires used for the connection to the PCB was a stranded type wire. This proved infective because after heating the wires while applying the melted solder, the mechanical properties of the wires decreased. As a result, the fragility of the wires increased and whenever the PCB was moved, the connections with the stranded wires were broken. To solve that issue, the change from stranded wires to solid core copper wires was made. With this, the stability of the system's connection to the PCB was improved and the system could be moved without concern for the chance of broken connections.

The last component fabricated was the valve regulation system which include solenoid valves, diodes, resistors and transistors. The valves were wired to a breadboard, which was further connected to the microcontroller (Arduino Uno). A PCB was not used, because there were concerns with the solenoid valves' weight affecting the wires and possibly breaking the connections. However, this issue can be easily remedied with further refinement in the design of the PCB. Transistors in the circuit were used as a switch to the valves, providing control over when to open and close the valves. The diodes were used a protection agent for the circuit. When power is eliminated from a valve, a voltage spike will occur. The diode protects the system from the spike and slowly dissipates the voltage so that no harm is caused to the system. Finally, the resistors are to reduce the current and voltage being allowed to the valves to protect the system from receiving an excessive amount of current and short-circuiting the system.

Alternative designs are also contemplated, such as connections from the controller unit to the valve regulation system can be such that the valve system is physically connected to the Raspberry Pi through jumper wires, or to a Bluetooth connection between the Raspberry Pi and another microcontroller (Arduino Uno). This modification allows more flexibility in how the user can setup the system and without being restricted by the length of physical wires, but rather, only restricted to the length of the wireless Bluetooth connection range.

Figure 10:
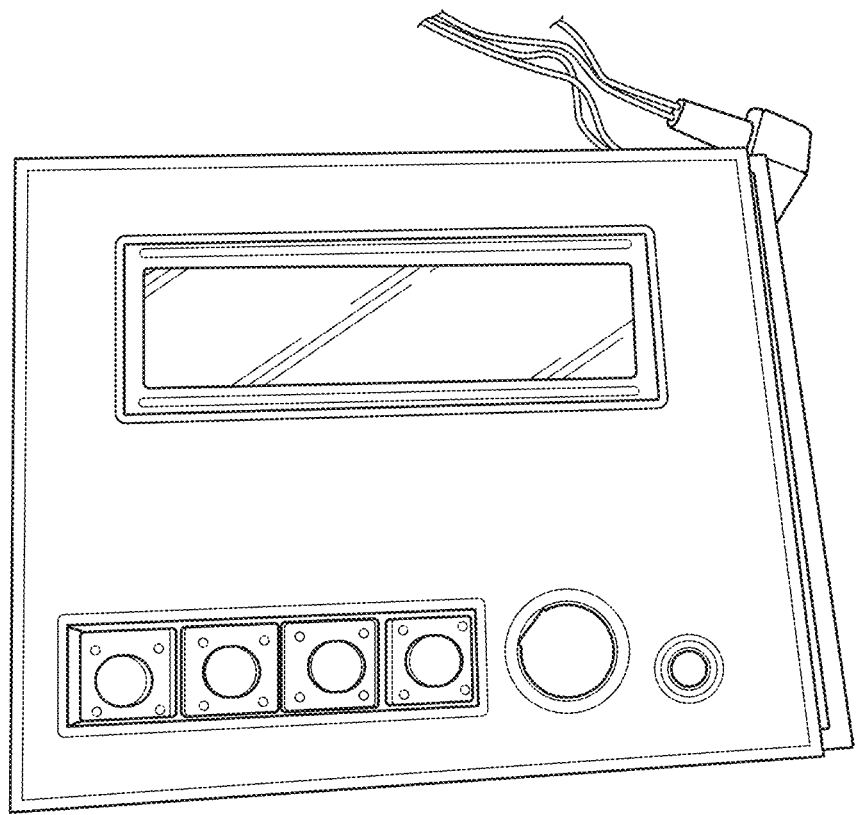
FIG. 10 is a picture of a front view of an assembled controller shown in FIG. 9.

The final assembly of the Raspberry Pi portion of the system included Raspberry Pi, the PCB, and the LCD housed within the housing unit as seen in FIG. 10. The Raspberry Pi, PCB, and LCD screen is secured into the housing unit by utilizing mounting screws in their respective pilot holes.

The final system assembly includes the hypoxic chamber, the Arduino valve component, the gas tanks, the Raspberry Pi, and the oxygen sensor. The housing unit for the Raspberry Pi is located next to the hypoxic chamber at allow the sensor to be wired into the chamber. The Arduino unit is located near the gas tanks with the valves and receives signals from the Raspberry Pi through Bluetooth to activate and deactivate the solenoid valves for the gas tanks.

Example 4

Performance Evaluation—Pre-Modifications

Figure 11:
FIG. 11 is a flowchart of performance validation process for measuring oxygen sensing delay.

The hypoxic chamber system described in Examples 1-3 was tested for oxygen sensing accuracy, and after an initial testing run it was determined that the oxygen reading on the LCD screen had a delay that after the gas inflow was stopped the percent of oxygen continued to decrease. To test for this percent delay, optimal hypoxic conditions, the testing followed the figure above (FIG. 11).

After initial testing using the validation process described in FIG. 11, data was compiled into the Tables 3-5 below.

TABLE 3

Data of 10 L/min testing for percent delay

| 10 L/min | Run 1 | Run 2 | Run 3 | Average | Std Dev |
| --- | --- | --- | --- | --- | --- |
| Start Percentage (%) | 19.97 | 20.09 | 20.07 | 20.04 | 0.064 |
| Stop Percentage (%) | 7.00 | 7.08 | 6.93 | 7.00 | 0.075 |
| Final Percentage (%) | 5.01 | 5.02 | 4.89 | 4.97 | 0.072 |
| Difference | 1.99 | 2.06 | 2.04 | 2.03 | 0.036 |
| Time (sec) Start - Stop | 56 + 1 | 56 + 1 | 57 + 1 | 56.18 + 1 | 0.610 |
| Time (sec) Stop - End | 52 + 1 | 57 + 1 | 57 + 1 | 55.23 + 1 | 3.156 |
| Total Time Elapsed | 108 + 1 | 113 + 1 | 114 + 1 | 111.41 + 1 | 3.645 |

TABLE 4

Data of 20 L/min testing for percent delay

| 20 L/min | Run 1 | Run 2 | Run 3 | Average | Std Dev |
| --- | --- | --- | --- | --- | --- |
| Start Percentage | 20.07 | 20.04 | 20.04 | 20.05 | 0.017 |
| Stop Percentage | 7.00 | 8.39 | 9.11 | 8.17 | 1.073 |
| Final Percentage | 3.45 | 4.17 | 4.53 | 4.05 | 0.550 |
| Difference | 3.55 | 4.22 | 4.58 | 4.13 | 0.524 |
| Time (sec) Start -Stop | 33 + 1 | 31 + 1 | 30 + 1 | 31.38 + 1 | 1.863 |
| Time (sec) Stop - End | 56 + 1 | 49 + 1 | 56 + 1 | 53.81 + 1 | 4.391 |
| Total Time Elapsed | 89 + 1 | 80 + 1 | 86 + 1 | 85.19 + 1 | 5.201 |

TABLE 5

Data of 30 L/min testing for percent delay

| 30 L/min | Run 1 | Run 2 | Run 3 | Average | Std Dev |
| --- | --- | --- | --- | --- | --- |
| Start Percentage | 20.04 | 20.02 | 20.08 | 20.05 | 0.031 |
| Stop Percentage | 9.09 | 10.22 | 11.31 | 10.21 | 1.110 |
| Final Percentage | 3.47 | 3.88 | 4.42 | 3.92 | 0.476 |
| Difference | 5.62 | 6.34 | 6.89 | 6.28 | 0.637 |
| Time (sec) Start -Stop | 24 + 1 | 21 + 1 | 19 + 1 | 20.88 + 1 | 2.467 |
| Time (sec) Stop - End | 67 + 1 | 55 + 1 | 66 + 1 | 62.67 + 1 | 6.490 |
| Total Time Elapsed | 90 + 1 | 76 + 1 | 85 + 1 | 83.55 + 1 | 7.306 |

From the data, the average percent delay was determined, as well as the time for the chamber to homogenize.

Based on the results from preliminary testing it was determined that the percent delay of decreasing oxygen was approximately 5% from initial atmospheric oxygen levels (~20%) at the flow rate the team desired. Based on the results of testing the team programmed a percent delay from the initial purge and would close the valve responsible for oxygen depletion at the max threshold set plus the percent delay determined. However, after secondary testing with the percent delay incorporated into the programming it was found that that the alert system was not in ideal working condition, because when the percent delay was incorporated, the buzzer alarm was activated at the thresholds and during the percent delay instead of only at deviations from the threshold. After discovering this error in the programming, a method to control gas flow accurately even when not doing an initial purge was needed.

Example 5

Performance Evaluation—Post-Modifications

After determining the problems with the previous settings programmed into the system in Example 4, an alternative solution to solve the initial purge delay was developed. The solution is to instruct the valves controlling the gases to only open for a short duration of time and then delay the system to allow the hypoxic chamber's gases to stabilize and homogenize before the oxygen concentration levels that are displayed on the LCD are constant for a significant period of time. This solution addresses the issue of triggering alerts outside the threshold, because of the initial purge oxygen percent delay.

Figure 12:
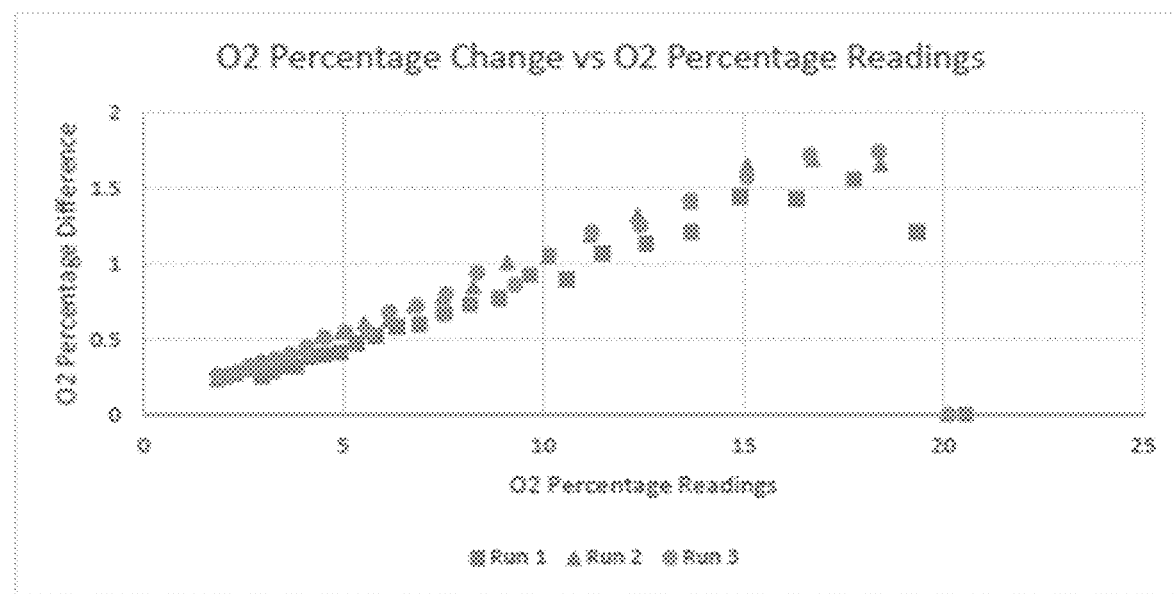
FIG. 12 is a graph of a percent delay in oxygen content changes verses oxygen percentage readings received from an oxygen sensor.

The data for the new percent delay were collected and compiled. The test runs had a flow pressure of 3 psi for the mixture of 5% carbon dioxide and 95% nitrogen. Results are presented in Table 6 and FIG. 12.

TABLE 6

Sample Data of new percent delay

| Run 1 | | | Run 2 | | | Run 3 | | |
| --- | --- | --- | --- | --- | --- | --- | --- | --- |
| Time | O$_2$ % | Diff | Time | O$_2$ % | Diff | Time | O$_2$ % | Diff |
| 0 | 20.54 | 0 | 0 | 20.08 | 0 | 0 | 20.12 | 0 |
| 50 | 19.33 | 1.21 | 62.36 | 18.42 | 1.66 | 68.51 | 18.38 | 1.74 |
| 51.92 | 17.77 | 1.56 | 56.22 | 16.73 | 1.69 | 59 | 16.66 | 1.72 |
| 52.62 | 16.34 | 1.43 | 63.12 | 15.08 | 1.65 | 64.64 | 15.09 | 1.57 |
| 59.5 | 14.9 | 1.44 | 59.65 | 13.67 | 1.41 | 60.43 | 13.67 | 1.42 |
| 54.52 | 13.69 | 1.21 | 59.3 | 12.35 | 1.32 | 67.69 | 12.42 | 1.25 |

Based on the data recorded from the testing runs, durations of time that the valves should be opened to deliver a small but significant amount of gas to the system were determined. Using the above described gases, the carbon dioxide nitrogen mix was optimally held open for two seconds and the oxygen valve open for only one second, since the oxygen canister contains 100% pure oxygen. This modification allows the system to slowly purge the system from the initial atmospheric oxygen concentrations to the set point provided from the user. One issue with the new programming is that the initial purge from atmospheric oxygen to the set point's oxygen level will be significantly longer than the time in the preliminary testing where the system was purged all at once and tried to reach the threshold region. However, since the system is automated, the time the system takes to reach the set point becomes less significant, because a user does not have to actively monitor the system, and only needs to be notified if the oxygen concentration levels significantly deviate from the preset oxygen concentration threshold.

In summary, described hypoxic chamber system uses a dual gas to allow for greater customization for the client instead of single gas systems. With a dual gas system, the user is able to change the oxygen concentrations to any percent that is wanted in comparison to single gas systems where the amount of oxygen in the system is usually fixed at a certain point. The hypoxic chamber system changes the oxygen concentration inside the chamber in small increments, waits for the gases inside the chamber to stabilize, and then releases more gas to further decrease or increase oxygen levels.

The invention claimed is:

1. A hypoxic chamber system comprising:
 a hypoxic chamber having:
  a housing,
  an internal receiving chamber formed within the housing,
  a lid operably connectable to the housing to seal the receiving chamber in a closed position,
  a release valve in communication with the receiving chamber,
  a first input and a second input in communication with the receiving chamber, and
  an oxygen sensor positioned in the receiving chamber;
 a first regulator valve operatively connected to the first input and an oxygen source;
 a second regulator valve operatively connected to the second input and a non-oxygen source; and
 a controller electrically connected to the first regulator valve, the second regulator valve, and the oxygen sensor,
 wherein the controller is programmed with a predetermined oxygen level,
 wherein the first regulator valve and second regulator valve are electronically actuated,
 wherein electronic actuation of the first regulator valve and the second regulator valve is controlled by the controller,
 wherein the controller electronically actuates the first regulator valve and/or the second regulator valve in response to oxygen sensor readings of an oxygen level in the receiving chamber,
 wherein the controller electronically actuates the first regulator valve to increase oxygen levels in the receiving chamber,
 wherein the controller electronically actuates the second regulator to decrease oxygen levels in the receiving chamber, and
 wherein the controller electronically actuates the first regulator valve upon oxygen levels in the internal receiving chamber being sensed by the oxygen sensor as being below the predetermined oxygen level, and actuates the second regulator valve upon oxygen levels in the internal receiving chamber being sensed by the oxygen sensor as being above the predetermined oxygen level.

2. The system of claim 1, wherein the first regulator valve and the second regulator valve are wireless controlled by the controller.

3. The system of claim 1, wherein the controller further comprises a graphic user interface.

4. The system of claim 3, wherein the graphic user interface is a touch screen or a display screen.

5. The system of claim 1, wherein the oxygen source is a tank comprising oxygen or an oxygen enriched gas.

6. The system of claim 1, wherein the non-oxygen source is a tank comprising nitrogen, carbon dioxide, or a combination thereof.

7. The system of claim 1, wherein the controller is programmable by a user to set a predetermined oxygen level in the internal receiving chamber.

8. The system of claim 1, wherein the controller continuously monitors oxygen levels in the internal receiving chamber with the oxygen sensor.

9. The system of claim 1, wherein the controller monitors oxygen levels in the internal receiving chamber with the oxygen sensor at predetermined time intervals.

10. The system of claim 1, wherein the controller further comprises an auditory or visual indicator that is activated when the oxygen sensor measures an oxygen level that exceeds or falls below the predetermined oxygen level.

11. The system of claim 1, wherein the hypoxic chamber and housing are formed from a thermoplastic polymer.

12. The system of claim 11, wherein the thermoplastic polymer is acrylonitrile butadiene styrene (ABS), a polycarbonate, or a combination of both.

13. The system of claim 11, wherein the thermoplastic polymer is structurally stable at 120° C. or greater for at least 30 minutes under saturated steam under at least 10 psi of pressure.

14. A method of growing cells in a hypoxic environment comprising:
 placing the cells in the receiving chamber of the hypoxic chamber system of claim 1;
 setting a predetermined oxygen level for the receiving chamber, and
 actuating the first regulator valve, second regulator valve, or both to introduce an environment in the receiving chamber having the predetermined oxygen level.

15. The method of claim 14, further comprising
 monitoring oxygen levels in the receiving chamber with the oxygen sensor;
 actuating the first regulator valve upon oxygen levels in the receiving chamber being sensed by the oxygen sensor as being below the predetermined oxygen level; and
 actuating the second regulator valve upon oxygen levels in the receiving chamber being sensed by the oxygen sensor as being above the predetermined oxygen level.

* * * * *